United States Patent
Yamaha et al.

(10) Patent No.: US 12,050,188 B2
(45) Date of Patent: Jul. 30, 2024

(54) STRENGTH EVALUATION DEVICE AND STRENGTH EVALUATION METHOD

(71) Applicant: IHI Corporation, Koto-ku (JP)

(72) Inventors: Sayo Yamaha, Tokyo (JP); Takahiro Fukumaru, Tokyo (JP); Yuichi Yamaguchi, Tokyo (JP)

(73) Assignee: IHI Corporation, Koto-ku (JP)

(*) Notice: Subject to any disclaimer, the term of this patent is extended or adjusted under 35 U.S.C. 154(b) by 393 days.

(21) Appl. No.: 17/441,944

(22) PCT Filed: Mar. 27, 2020

(86) PCT No.: PCT/JP2020/014142
§ 371 (c)(1),
(2) Date: Sep. 22, 2021

(87) PCT Pub. No.: WO2020/196855
PCT Pub. Date: Oct. 1, 2020

(65) Prior Publication Data
US 2022/0163434 A1    May 26, 2022

(30) Foreign Application Priority Data
Mar. 27, 2019 (JP) .................. 2019-061232

(51) Int. Cl.
*G01N 23/046* (2018.01)
*G01N 3/08* (2006.01)
(Continued)

(52) U.S. Cl.
CPC ............. *G01N 23/046* (2013.01); *G01N 3/08* (2013.01); *B32B 5/02* (2013.01); *G01B 15/02* (2013.01); *G01N 2021/8444* (2013.01)

(58) Field of Classification Search
CPC .......... G01N 3/08; G01N 23/00; G01N 23/02; G01N 23/04; G01N 23/046;
(Continued)

(56) References Cited

U.S. PATENT DOCUMENTS

2011/0135872 A1   6/2011   May et al.
2016/0247271 A1   8/2016   Hishida et al.
(Continued)

FOREIGN PATENT DOCUMENTS

DE   10 2015 216 015 A1   2/2017
EP       2 572 871 A2      3/2013
(Continued)

OTHER PUBLICATIONS

Shunya Fukushige, et al., "Strength Analysis for Cornposites with Fiber Waviness," The 30th Computational Mechanics Conference, The Japan Society of Mechanical Engineers, Sep. 2017, 3 pages (with English Abstract).

*Primary Examiner* — Benjamin R Schmitt
(74) *Attorney, Agent, or Firm* — Oblon, McClelland, Maier & Neustadt, L.L.P.

(57) ABSTRACT

A strength evaluation method is a strength evaluation method for a composite material in which a plurality of fiber layers are laminated and includes a meandering state measuring process of measuring a meandering state of fibers of the plurality of fiber layers in a direction along the fiber layers, a meandering thickness measuring process of measuring a meandering thickness that is a thickness in a lamination direction of a part in which meanderings of fibers of the plurality of fiber layers occur, and a strength evaluation process of evaluating a strength of the composite material based on the meandering state and the meandering thickness.

9 Claims, 4 Drawing Sheets

(51) Int. Cl.
*B32B 5/02* (2006.01)
*G01B 15/02* (2006.01)
*G01N 21/84* (2006.01)

(58) Field of Classification Search
CPC ......... G01N 2021/8444; G01N 33/442; G01N 2223/419; G01N 2223/615; G01B 15/02; B32B 5/02
See application file for complete search history.

(56) References Cited

U.S. PATENT DOCUMENTS

| | | |
|---|---|---|
| 2016/0349193 A1 | 12/2016 | Guenter et al. |
| 2019/0072521 A1 | 3/2019 | Kawai et al. |
| 2020/0024414 A1 | 1/2020 | Ichino et al. |

FOREIGN PATENT DOCUMENTS

| | | | |
|---|---|---|---|
| EP | 3 431 981 A1 | 1/2019 | |
| JP | 4-306240 A | 10/1992 | |
| JP | 2008-122178 A | 5/2008 | |
| JP | 2017-507327 A | 3/2017 | |
| JP | 2018-159691 A | 10/2018 | |
| KR | 20170125008 A * | 11/2017 | ............... C08J 5/04 |
| WO | WO 2010/147231 A1 | 12/2010 | |
| WO | WO 2015/046534 A1 | 4/2015 | |
| WO | WO 2017/158864 A1 | 9/2017 | |
| WO | WO 2018/181983 A1 | 10/2018 | |

* cited by examiner

STRENGTH EVALUATION DEVICE AND STRENGTH EVALUATION METHOD

TECHNICAL FIELD

The present disclosure relates to a strength evaluation device and a strength evaluation method.

The present application is a National Stage entry of PCT/JP2020/014142 filed on Mar. 27, 2020, which claims priority to Japanese Patent Application No. 2019-061232, filed Mar. 27, 2019, the content of which is incorporated herein by reference.

BACKGROUND

In a composite material formed by laminating fibers (fiber layers), it is considered that the meandering of fibers generated along a fiber layer (a prepreg) affects the strength of the composite material. It is considered that such meandering of fibers occurs, for example, in a manufacturing stage, at the time of pressure molding, at the time of arranging fibers, and the like. For example, Patent Literature 1 discloses a method for quantitatively evaluating the meandering state of fibers of a fiber-reinforced composite material.

Document of Related Art

Patent Document

[Patent Document 1] Japanese Unexamined Patent Application, First Publication No. 2018-159691

SUMMARY

Technical Problem

Incidentally, the meandering of fibers along such a fiber layer may spread to other fiber layers adjacent to the fiber layer in a lamination direction, and similar fiber meandering may occur at a plurality of positions on laminated fiber layers. However, at present, only the meandering state in a direction along the fiber layer is considered, and it may be difficult to properly evaluate the strength of a composite material from the meandering state.

The present disclosure is made in view of the problems described above and an object thereof is to evaluate the strength of a composite material based on the meandering state thereof.

Solution to Problem

According to a first aspect of the present disclosure, a strength evaluation method for a composite material in which a plurality of fiber layers are laminated includes a meandering state measuring process of measuring a meandering state of fibers of the plurality of fiber layers in a direction along the fiber layers, a meandering thickness measuring process of measuring a meandering thickness that is a thickness in a lamination direction of a part in which meanderings of fibers of the plurality of fiber layers occur, and a strength evaluation process of evaluating a strength of the composite material based on the meandering state and the meandering thickness.

According to a second aspect of the present disclosure, in the first aspect, in the meandering state measuring process, meandering amplitudes of the fibers of the fiber layers are measured, and a maximum value of the meandering amplitudes is used as a maximum amplitude, and in the strength evaluation process, the strength is evaluated based on the maximum amplitude and the meandering thickness.

According to a third aspect of the present disclosure, in the first or second aspect, in the meandering thickness measuring process, the number of laminations of the meandering fibers of the composite material is measured as the meandering thickness.

According to a fourth aspect of the present disclosure, in any one of the first to third aspects, in the strength evaluation process, a reciprocal number of a product value of the meandering state and the meandering thickness is used as an evaluation parameter.

According to a fifth aspect of the present disclosure, a strength evaluation device for a composite material in which a plurality of fiber layers are laminated includes a meandering state calculator calculate a meandering state of fibers of the plurality of fiber layers in a direction along the fiber layers, a meandering thickness calculator calculate a meandering thickness that is a thickness in a lamination direction of a part in which meanderings of fibers of the plurality of fiber layers occur, and a strength evaluator evaluate a strength of the composite material based on the meandering state and the meandering thickness.

Effects

According to the present disclosure, it is possible to evaluate meandering after considering a meandering state in a direction along fiber layers and a spread state of meandering in the lamination direction by evaluating a strength based on the meandering state and a meandering thickness. Therefore, in the present disclosure, it is possible to appropriately evaluate the strength after considering the meandering states in both the direction along fiber layers and the lamination direction.

DESCRIPTION OF EMBODIMENTS

Hereinafter, an embodiment of the strength evaluation method and the strength evaluation device according to the present disclosure will be described with reference to the drawings.

Figure 1:
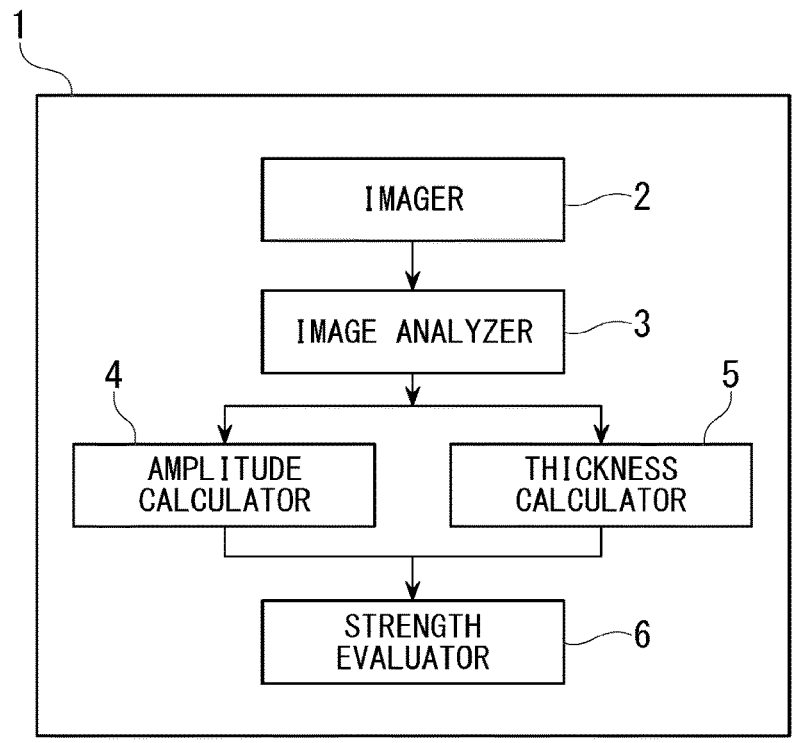
FIG. 1 is a block diagram which shows a functional configuration of a strength evaluation device according to one embodiment of the present disclosure.

A strength evaluation device 1 according to the present embodiment is a device that evaluates the strength of a composite material bonded by a resin in a state where a plurality of fiber layers are laminated. Such a composite material is pressed in a state of being impregnated with a resin after the fiber layers are laminated, so that fibers of each fiber layer may meander in a direction along the fiber layer. The "direction along the fiber layer" means a direction orthogonal to a lamination direction (a thickness direction) of the plurality of fiber layers. In addition, it is also known that meanderings in the direction along the fiber layers of the fibers of a composite material occur in parallel in a plurality of fiber layers adjacent to each other in the lamination direction. The strength evaluation device 1 evaluates the strength based on the meanderings of the fibers of the composite material. As shown in FIG. 1, the strength evaluation device 1 includes an imager 2, an image analyzer 3, an amplitude calculator 4 (a meandering state calculator), a thickness calculator 5 (a meandering thickness calculator), and a strength evaluator 6. The image analyzer 3, the amplitude calculator 4, the thickness calculator 5, and the strength evaluator 6 are considered to be one function of a computer, and function in association with a central processing unit (CPU), a storage medium, and output devices such as a monitor.

The image analyzer 3, the amplitude calculator 4, the thickness calculator 5, and the strength evaluator 6 may be configured from a plurality of computers, or each may also be configured from a single computer. Such a computer may be configured from a CPU, a memory such as a random access memory (RAM) or a read only memory (ROM), a storage device such as a solid state drive (SSD) and a hard disk drive (HDD), and an input and output device that exchanges signals with a device such as the imager 2 or a sensor.

The imager 2 is a device that captures an image of a composite material by X-ray computed tomography (CT). The imager 2 scans the composite material using X-rays and non-destructively acquires an internal structure of the composite material as a captured image. The imager 2 includes an X-ray generator, an X-ray detector, and the like.

Figure 2:
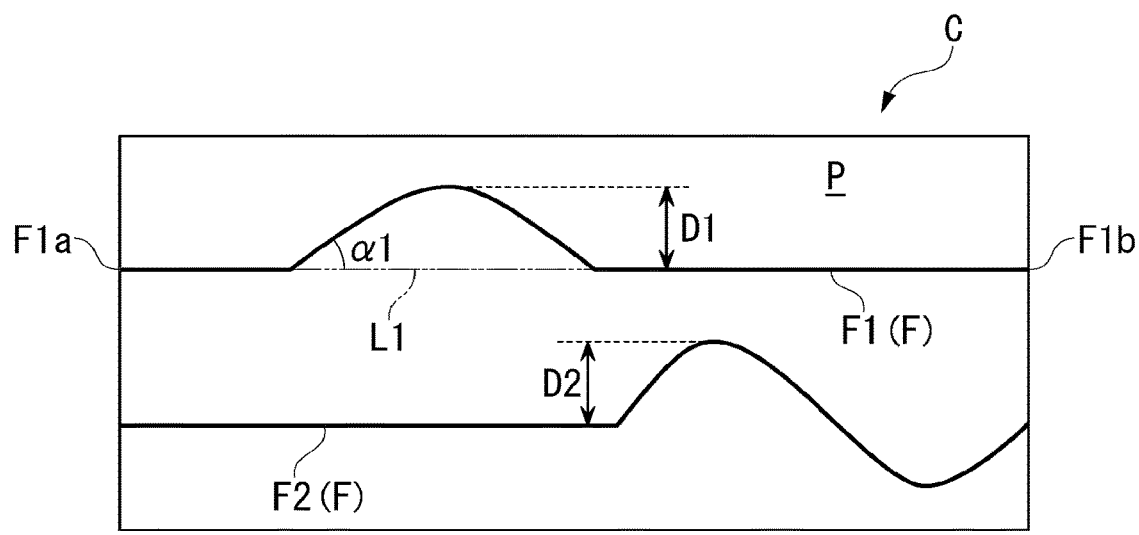
FIG. 2 is a schematic diagram which shows meandering of a composite material and fibers.

The image analyzer 3 acquires a plurality of images of the composite material captured by the imager 2 and extracts contour of the composite material in a three-dimensional direction and contours of the fibers from the images. Then, the image analyzer 3 detects, from the contours of the fibers, the meanderings of fibers F (F1, F2) in a fiber layer P of a composite material C as shown in FIG. 2, that is, a state in which the fibers F are arranged to be curved instead of having a linear shape. Note that FIG. 2 shows a plan view of a single fiber layer P (a view viewed in the thickness direction), but the composite material C is configured by a plurality of fiber layers P being laminated in the thickness direction.

As shown in FIG. 2, the amplitude calculator 4 calculates amplitudes (the meandering amplitudes) of the meandering fibers based on the contours of fibers analyzed by the image analyzer 3 and the detected meandering state of the fibers. In the composite material, a plurality of fiber meanderings may occur. In this case, the amplitude calculator 4 extracts the maximum value (the maximum amplitude) of a meandering amplitude generated in the plurality of fiber layers, and stores a position (coordinates) of a fiber where the meandering amplitude is a maximum.

The thickness calculator 5 identifies fiber layers of the detected composite material based on the contour of the composite material analyzed by the image analyzer 3. Then, the thickness calculator 5 calculates the number of fiber layers affected by a meandering portion having the maximum amplitude among the meanderings of fibers detected by the image analyzer 3, that is, the number of fiber layers (a thickness in the lamination direction) in which similar meandering occurs in parallel. Also, the number of fiber layers may be referred to as "a number of laminations of fibers", and "a meandering thickness".

The strength evaluator 6 acquires the meandering amplitude (a meandering state) and the number of fiber layers (a meandering thickness) from the amplitude calculator 4 and the thickness calculator 5, and stores, as an evaluation parameter, a reciprocal number of a product value of the meandering amplitude and the number of fiber layers. In addition, the strength evaluator 6 stores a map based on a correlation (refer to FIG. 4) between a strength (for example, a tensile strength) and an evaluation parameter calculated in advance by experiments or the like. The strength evaluator 6 refers to such a map and estimates the strength of a composite material from the measured evaluation parameter.

Figure 3:
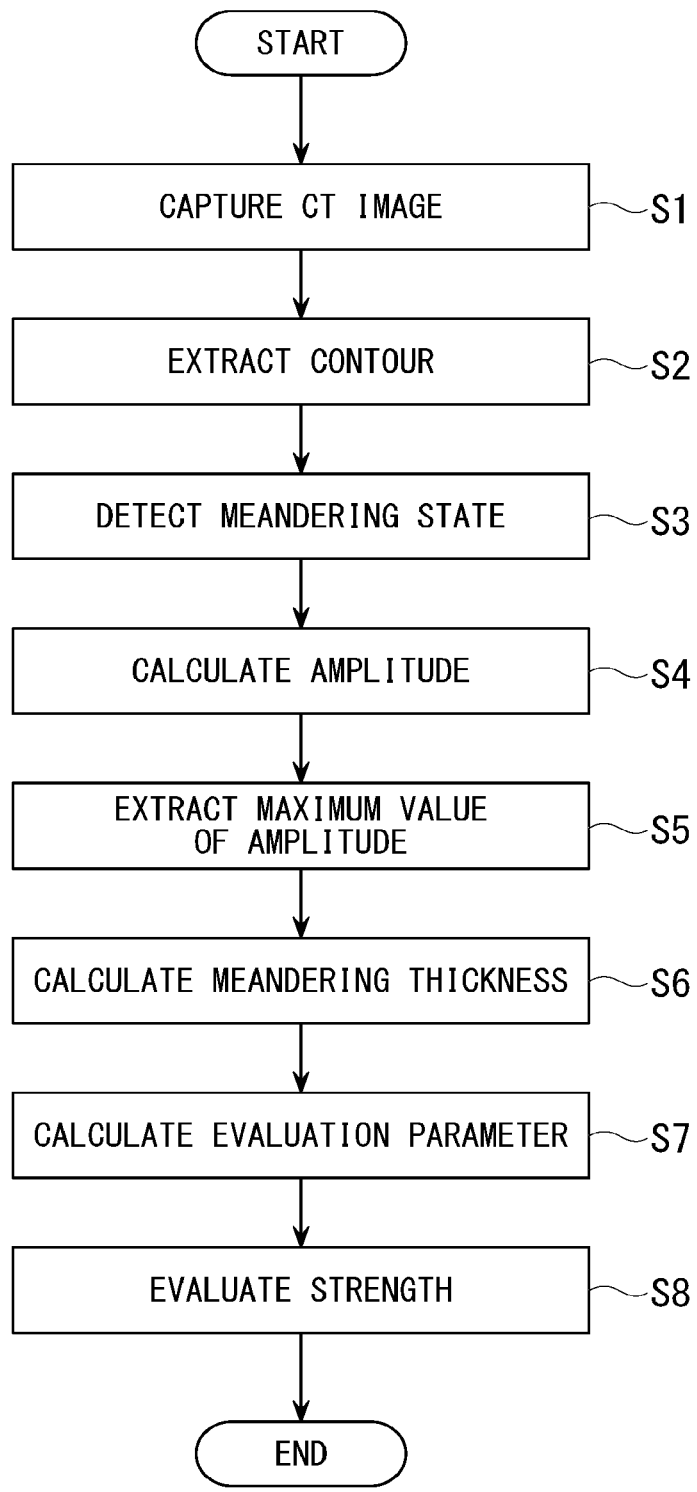
FIG. 3 is a flowchart which shows a strength evaluation method according to one embodiment of the present disclosure.

Subsequently, the strength evaluation method according to the present embodiment will be described with reference to FIG. 3.

First, the strength evaluation device 1 according to the present embodiment performs X-ray CT imaging of the composite material at the imager 2 (step S1). At this time, a structure of the composite material is three-dimensionally acquired by the imager 2, including the internal structure. Then, the strength evaluation device 1 extracts the contour of an outer shape of the composite material and the contours of the fibers from a CT image at the image analyzer 3 (step S2). The image analyzer 3, for example, binarizes the captured CT image and determines a portion exceeding a predetermined threshold value as a contour of the outer shape of the composite material and the contours of the fibers. Furthermore, the strength evaluation device 1 detects the meandering state of fibers from the contours of the fibers at the image analyzer 3 (step S3).

Then, as shown in FIG. 2, the strength evaluation device 1 calculates the amplitudes (the meandering amplitudes) of the detected meandering fibers based on the contours of the fibers at the amplitude calculator 4 (step S4). Furthermore, the strength evaluation device 1 extracts the maximum value (the maximum amplitude) of the calculated meandering amplitudes at the amplitude calculator 4 (step S5). In addition, in this case, the amplitude calculator 4 stores coordinates (three-dimensional position coordinates) of a fiber where the meandering amplitude is a maximum. Note that steps S4 and S5 correspond to the meandering state measuring process in the present disclosure.

Although there are a plurality of methods for calculating the meandering amplitude, for example, as shown in FIG. 2, a distance D1 (a distance along the fiber layer P and in a direction orthogonal to a straight line L1) of one fiber F1 from the virtual straight line L1 connecting both ends F1a and F1b in an imaging region of the imager 2 to a farthest away portion of the meandering fiber F1 may be used as the meandering amplitude. In addition, local meanderings of fibers are important for evaluating the strength of the composite material C, but, for example, since fiber curvature based on a shape of the composite material C may be excluded from the strength evaluation as a normally possible curvature, an arc which best approximates a locus of one fiber in the imaging area of the imager 2 and is represented by a single radius may be derived, and a distance from the arc to the farthest away portion of the meandering fiber may be used as the meandering amplitude.

Furthermore, as shown in FIG. 2, when meandering occurs in a plurality of fibers F1 and F2, the distances D1 and D2 indicating the meandering amplitudes may be calculated, respectively, and a larger distance between the distances D1 and D2 may be used as the maximum amplitude.

Next, the strength evaluation device 1 calculates the number of fiber layers (the meandering thickness) over which meanderings spread at the thickness calculator 5 (step S6). At this time, the thickness calculator 5 extracts whether meandering is detected at the same position in each fiber layer (the same position in a two-dimensional direction along the fiber layer) as a position of a portion of a fiber where the meandering amplitude is a maximum. Then, when meanderings are detected at the same positions in a plurality of fiber layers adjacent to each other, it is assumed that the meanderings of fibers spread in the lamination direction, and the number of fiber layers from which the spread of meanderings are extracted is calculated. Note that step S6 corresponds to a meandering thickness measuring process in the present disclosure.

Then, the strength evaluation device 1 calculates an evaluation parameter at the strength evaluator 6 (step S7). At this time, the strength evaluator 6 acquires the maximum value of the meandering amplitude calculated by the amplitude calculator 4 and the number of fiber layers calculated by the thickness calculator 5, and calculates a reciprocal number of a product of the maximum value and the number of fiber layers described above as an evaluation parameter.

Furthermore, the strength evaluation device 1 evaluates the strength of the composite material at the strength evaluator 6 (step S8). In this case, the strength evaluator 6 stores a map based on a correlation between a tensile strength and an evaluation parameter, and derives the tensile strength from the evaluation parameter calculated in step S7 based on the map described above. Note that steps S7 and S8 correspond to the strength evaluation process in the present disclosure.

Figure 5A:
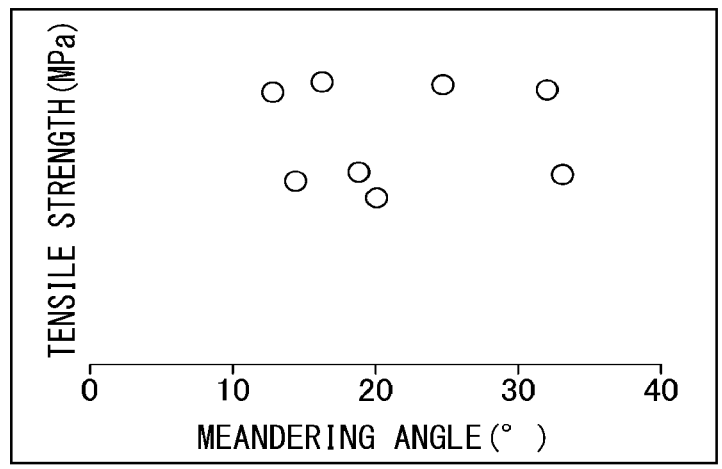
FIG. 5A is a graph which shows a relationship between a meandering angle and the tensile strength.
Figure 5B:
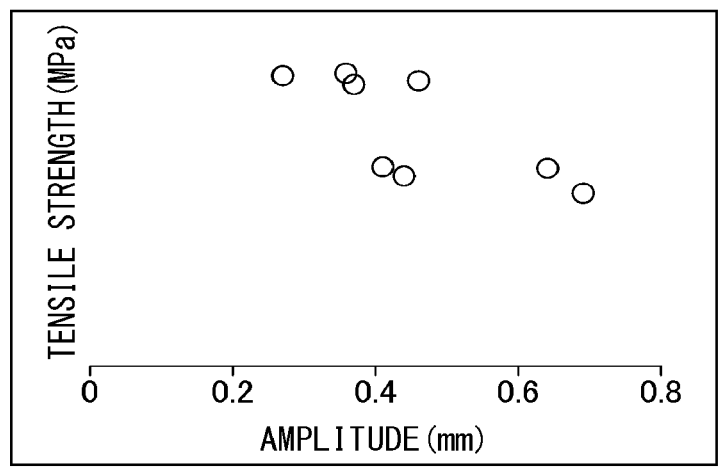
FIG. 5B is a graph which shows a relationship between a meandering amplitude and the tensile strength.
Figure 5C:
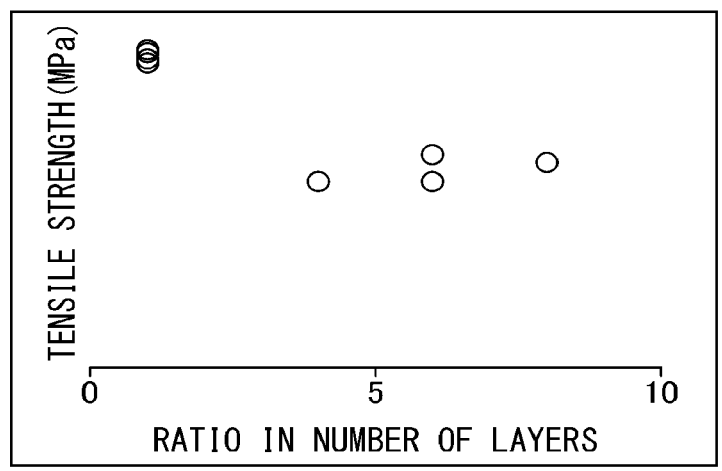
FIG. 5C is a graph which shows a relationship between a ratio of the number of meandering fiber layers to the total number of layers and the tensile strength.

The correlation between the evaluation parameter and the tensile strength in the present embodiment will be described. FIG. 5A is a graph showing a relationship between a meandering angle and the tensile strength, FIG. 5B is a graph showing a relationship between the meandering amplitude and the tensile strength, and FIG. 5C is a graph showing a relationship between a ratio of the number of meandering fiber layers to the total number of layers and the tensile strength.

The meandering angle refers to, for example in FIG. 2, the maximum angle α1 between the virtual straight line L1 and a place where the fiber F1 is meandering.

If the graph in FIG. 5A is viewed, it can be known that there is no correlation between the tensile strength and the meandering angle (an angle formed between a meandering fiber and a non-meandering fiber). Similarly, if the graph in FIG. 5B is viewed, there is no correlation between the tensile strength and the meandering amplitude. Moreover, if the graph in FIG. 5C is viewed, there is no correlation between the tensile strength and a ratio in the number of fiber layers.

That is, it is difficult to evaluate the tensile strength from the meandering angle and meandering amplitude, which are parameters focusing only on a meandering state in the direction along the fiber layer. Similarly, it is difficult to evaluate the tensile strength from the ratio in the number of layers, which is a parameter focusing only on a meandering state in the lamination direction.

Figure 4:
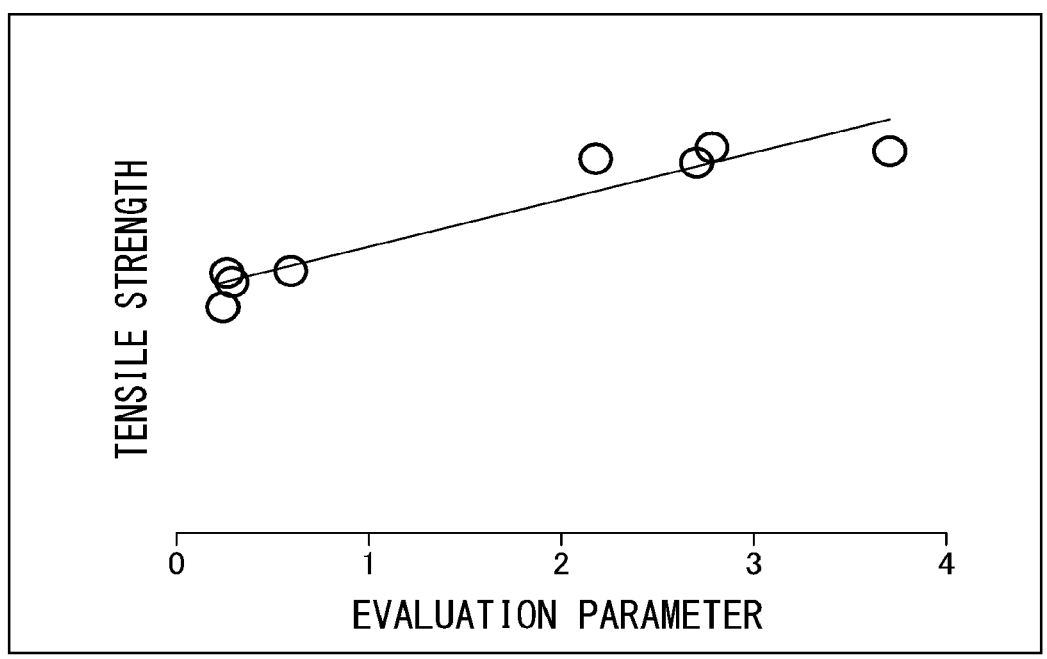
FIG. 4 is a graph which shows a correlation between an evaluation parameter and a tensile strength in the one embodiment of the present disclosure.

On the other hand, as shown in FIG. 4, the evaluation parameter in the present embodiment has a strong correlation with the tensile strength, and the tensile strength can be evaluated by calculating the evaluation parameter. That is, the evaluation parameter in the present embodiment focuses on the meandering states in both the direction along the fiber layer and the lamination direction, and the evaluation of the tensile strength can be appropriately performed.

Moreover, the evaluation parameter in the present embodiment is calculated by using the maximum amplitude among the meandering amplitudes. Therefore, it is possible to evaluate the fiber meandering that has the greatest effect on all fiber layers.

Although the preferred embodiments of the present disclosure have been described above with reference to the drawings, the present disclosure is not limited to the embodiment described above. Various forms and combinations of the constituent members shown in the embodiment described above are examples, and various changes based on design requirements and the like can be made within the scope of the present disclosure.

In the embodiment described above, the thickness calculator 5 calculates the thickness of meandering fiber layers, but the present disclosure is not limited thereto. The thickness calculator 5 may calculate a fiber layer ratio obtained by dividing the thickness of the meandering fiber layers by the thickness of entire fiber layers, and may set this fiber layer ratio as the "meandering thickness" of the present disclosure. Then, the strength evaluator 6 calculates the evaluation parameter based on the fiber layer ratio and the maximum amplitude. In this case, even when various composite materials whose entire fiber layers have significantly different thicknesses are evaluated, strength evaluation can be performed using one map without being affected by the thicknesses of fiber layers.

In addition, in the embodiment described above, it is assumed that the amplitude calculator 4 calculates the meandering amplitude, but the present disclosure is not limited thereto. For example, the strength evaluation device 1 may not include the amplitude calculator 4 but may include a meandering angle calculator. The meandering angle calculator calculates the meandering angle in the fiber layer. At this time, the strength evaluator 6 calculates the evaluation parameter based on the meandering angles and the number of meandering fiber layers in entire fiber layers. In this case as well, it is possible to evaluate the strength after paying attention to both the direction along the fiber layer and the lamination direction.

Moreover, the meandering angle calculator described above sets a maximum angle among a plurality of meandering angles as the maximum meandering angle, and the strength evaluator 6 may evaluate the strength of a composite material based on the maximum meandering angle and the meandering thickness (the number of fiber layers and the ratio in the fiber layers). Furthermore, the reciprocal number of a product of the maximum meandering angle and the meandering thickness may be used as an evaluation parameter.

Moreover, in the embodiment described above, it is assumed that the thickness calculator 5 calculates the number of fiber layers, but the present disclosure is not limited thereto. For example, the thickness calculator 5 may calculate the thickness of fiber layers in millimeter or micrometer.

Moreover, in the above embodiment, it is assumed that the strength evaluation device 1 executes a strength evaluation method, but the present disclosure is not limited thereto. In the strength evaluation method according to the present disclosure, an operator may calculate an evaluation parameter based on a meandering thickness and one of a meandering amplitude and meandering angle that are manually measured, and, furthermore, evaluate the strength from the evaluation parameter. In this case, the strength may also be evaluated by using an approximate expression derived from a graph of the strength and the evaluation parameter created by conducting an experiment in advance instead of using a map for the strength evaluation.

In addition, in the embodiment described above, it is assumed that the strength evaluation device 1 includes the imager 2, but the present disclosure is not limited thereto. For example, the strength evaluation device 1 may not include the imager 2 and may acquire a CT image of a composite material captured externally and analyze the image.

Moreover, in the above embodiment, it is assumed that the tensile strength is evaluated, but the present disclosure is not limited thereto. For example, a map or an approximate expression may be derived for a bending strength in the same manner, and used for the evaluation of the bending strength.

In addition, the present disclosure may also include the following aspects.

In a sixth aspect of the present disclosure, a strength evaluation method for a composite material in which a plurality of fibers are laminated includes a meandering state measuring process of measuring a meandering state of fibers in a direction along a fiber layer, and a meandering thickness measuring process of measuring a meandering thickness, which is a thickness in the lamination direction of portions where meanderings of the fibers occur, and a strength evaluation process for evaluating a strength of the composite material based on the meandering state and the meandering thickness.

In a seventh aspect of the present disclosure, a strength evaluation device (1) of a composite material in which a plurality of fibers are laminated includes a meandering state calculator (4) that calculates a meandering state of the fibers in a direction along a fiber layer, a meandering thickness calculator (5) that calculates a meandering thickness, which is a thickness in the lamination direction of portions where meanderings of the fibers occur, and a strength evaluator (6) that evaluates the strength of the composite material based on the meandering state and the meandering thickness.

INDUSTRIAL APPLICABILITY

The present disclosure can be used in a strength evaluation device and a strength evaluation method for evaluating the strength of a composite material.

The invention claimed is:

1. A strength evaluation method for a composite material in which a plurality of fiber layers are laminated, the method comprising:
   a meandering state measuring process of measuring a meandering state of fibers of the plurality of fiber layers in a direction along the fiber layers by X-ray computed tomography;
   a meandering thickness measuring process of measuring a meandering thickness that is a thickness in a lamination direction of a part in which meanderings of fibers of the plurality of fiber layers occur by the X-ray computed tomography, and
   a strength evaluation process of evaluating a strength of the composite material based on the meandering state and the meandering thickness.

2. The strength evaluation method according to claim 1, wherein in the meandering state measuring process, meandering amplitudes of the fibers of the fiber layers are measured, and a maximum value of the meandering amplitudes is used as a maximum amplitude, and
   in the strength evaluation process, the strength is evaluated based on the maximum amplitude and the meandering thickness.

3. The strength evaluation method according to claim 2, wherein in the meandering thickness measuring process, a number of laminations of the meandering fibers of the composite material is measured as the meandering thickness.

4. The strength evaluation method according to claim 3, wherein in the strength evaluation process, a reciprocal number of a product value of the meandering state and the meandering thickness is used as an evaluation parameter.

5. The strength evaluation method according to claim 2, wherein in the strength evaluation process, a reciprocal number of a product value of the meandering state and the meandering thickness is used as an evaluation parameter.

6. The strength evaluation method according to claim 1, wherein in the meandering thickness measuring process, a number of laminations of the meandering fibers of the composite material is measured as the meandering thickness.

7. The strength evaluation method according to claim 6, wherein in the strength evaluation process, a reciprocal number of a product value of the meandering state and the meandering thickness is used as an evaluation parameter.

8. The strength evaluation method according to claim 1, wherein in the strength evaluation process, a reciprocal number of a product value of the meandering state and the meandering thickness is used as an evaluation parameter.

9. A strength evaluation device for a composite material in which a plurality of fiber layers are laminated, the device comprising:
   at least one memory storing instructions; and
   at least one processor configured, by executing the instructions, to:
   calculate a meandering state of fibers of the plurality of fiber layers in a direction along the fiber layers based on images acquired by X-ray computed tomography;
   calculate a meandering thickness that is a thickness in a lamination direction of a part in which meanderings of fibers of the plurality of fiber layers occur based on images acquired by the X-ray computed tomography; and
   evaluate a strength of the composite material based on the meandering state and the meandering thickness.

\* \* \* \* \*